United States Patent [19]
Fischer

[11] Patent Number: 5,697,903
[45] Date of Patent: Dec. 16, 1997

[54] METHODS AND APPARATUS FOR DISPENSING COMPOSITIONS

[75] Inventor: Dan E. Fischer, Sandy, Utah

[73] Assignee: Ultradent Products, Inc., South Jordan, Utah

[21] Appl. No.: 603,927

[22] Filed: Feb. 22, 1996

[51] Int. Cl.$^6$ .................................................. A61M 5/00
[52] U.S. Cl. ............................ 604/82; 604/83; 604/87
[58] Field of Search ............................. 604/218, 86, 88, 604/82, 220, 187, 83, 56, 87

[56] References Cited

U.S. PATENT DOCUMENTS

4,958,622  9/1990  Selenke ................................. 128/765

*Primary Examiner*—John D. Yasko
*Attorney, Agent, or Firm*—Workman Nydegger Seeley

[57] ABSTRACT

A syringe is provided for dispensing single and multi-component compositions while minimizing the entrainment of air. The syringe includes a barrel having a nozzle positioned at one end, a plunger slidably received in the other end, and a sidewall extending between the ends. The barrel has an interior surface defining a chamber for holding the composition. An access port extends through the sidewall to communicate with the chamber. The access port is positioned and configured so that the composition can initially be delivered though the access port and into the chamber near the nozzle. A sufficient amount of composition is positioned to fill the chamber up to the access port. When multi-component compositions are used, an elongated paddle is provided for insertion into the chamber through the second end of the barrel to facilitate mixing of the components within the chamber. As the paddle is removed, a scraper is provided for removing the composition from off the paddle. Once the composition is properly positioned, the plunger is advanced so as to push the air within the chamber out through the access port and to deliver the composition out through the nozzle.

21 Claims, 5 Drawing Sheets

METHODS AND APPARATUS FOR DISPENSING COMPOSITIONS

BACKGROUND OF THE INVENTION

1. The Field of the Invention

The present invention relates to methods and apparatus for use in dispensing single or multiple component compositions, such as dental cements or impression materials. More particularly, the present invention is directed to methods and apparatus for dispensing compositions so that the compositions are substantially free from entrained air.

2. The Relevant Technology

To properly place and use different compositions, it is often necessary to initially place the composition in a syringe. In the dental field, for example, it can be very helpful to initially place cements or binding agents in a syringe. The syringe can then be used to accurately position the binding agent for proper placement of a dental cap or other dental structure.

The use of a conventional syringe for delivery of a composition, however, can create problems. A conventional syringe has a nozzle end and an opposing loading end having a plunger slidably positioned therein. To fill the syringe with the composition, the plunger is removed and the composition is inserted into the syringe at the loading end. Removal of the plunger, however, can jeopardize the sterility of the plunger. This is because the plunger must typically be set down to enable proper loading of the syringe with the composition.

Once the composition is placed in the syringe, the plunger is inserted back into the loading end of the syringe. The plunger is then used to push the composition out the nozzle end. As the plunger is reinserted within the syringe, however, air can become trapped between the plunger and the composition. When low viscosity compositions are used, it is possible to orient the syringe so that the air within the syringe travels to the nozzle end where the air can be removed prior to dispersement of the composition. When high viscosity compositions are used, however, the air remains trapped. As the plunger is advanced, the air becomes entrained, forming air bubbles within the composition.

Depending on the composition and its intended use, the presence of air bubbles can have a detrimental affect. For example, when cements are used in the dental field, such as in bonding dental caps, air bubbles in the composition can produce an irregularity in the flow of the composition from the syringe and can also result in an uneven placement of the composition on the desired surface. As a result of the uneven placement, the cap may not be uniformly secured and thus have a weaker long term bond. The presence of air bubbles can also affect the setting rate of the composition. That is, the portion of the composition exposed to the air bubbles may begin setting more quickly than the remaining portion of the composition. This uneven setting can also influence the resulting effectiveness of the composition.

OBJECTS AND BRIEF SUMMARY OF THE INVENTION

Accordingly, it is a primary object of the present invention to provide improved methods and apparatus for dispensing compositions.

Another object of the present invention is to provide methods and apparatus for dispensing compositions from a syringe.

A further object of the present invention is to provide methods and apparatus for easily positioning the composition within a syringe.

Yet another object of the present invention is to provide methods and apparatus for dispensing compositions from a syringe without having to remove and potentially contaminate the plunger.

Another object of the present invention is to provide improved methods and apparatus for dispensing compositions from a syringe that substantially prevent the entrainment of air bubbles in the compositions.

It is a further object of the present invention to provide improved methods and apparatus for mixing and dispensing multi-component compositions.

Another object of the present invention is to provide methods and apparatus for mixing multi-component compositions which effect rapid and thorough mixing.

Yet another object of the present invention is to provide methods and apparatus for mixing a composition directly in a syringe so as to avoid having to transfer the composition from another location.

A further object of the present invention is to provide improved methods and apparatus for mixing multi-component compositions that substantially prevent the entrainment of air bubbles in the mixed compositions.

Finally, another object of the present invention is to provide improved methods and apparatus for dispensing highly viscous compositions from a syringe without trapping air between the plunger and the composition.

Additional objects and advantages of the invention are set forth hereinbelow in the detailed description, or will be appreciated by the practice of the invention.

To achieve the foregoing objects, and in accordance with the invention as embodied and broadly described herein, the present invention provides a novel syringe having an elongated barrel for holding and dispensing a composition. The barrel has a first or distal end, an open second or proximal end opposite the first end, and a sidewall extending between the first end and the second ends. The sidewall has an exterior surface and an interior surface. The interior surface defines a chamber for holding the composition.

An access port extends through the sidewall of the barrel to communicate with the chamber. The access port is configured so that the composition can be delivered through the access port and into the chamber at the distal end of the chamber. By using the access port, the composition can be positioned within the chamber without having to remove and potentially contaminate the plunger. Furthermore, since the access port is closer to the first end of the barrel, use of the access port makes it easier to position the composition within the barrel, beginning at the first or distal end of the barrel and then filling the barrel with composition from the distal end and working back toward the access port. In the preferred embodiment, a sufficient amount of the composition is added so as to fill the chamber up to the access port. The exact position of the access port along the longitudinal dimension of the barrel depends on the unit dose of composition that is desired to be dispensed from the syringe.

Once the composition is appropriately positioned within the chamber, the plunger can be advanced towards the first end of the barrel. As the plunger is advanced, the air between the plunger and the composition is pushed out the chamber through the access port. Once the plunger passes the access port, the remaining composition is pushed out a nozzle located at the first end of the barrel. Having the composition filled to the access port prevents air from being trapped between the plunger and the access port.

In applications requiring multi-component compositions, the components are placed in side-by-side orientation within the chamber, rather than one on top of another, to enable optimal mixing of the components. Once the components are positioned within the chamber, a mixing paddle is inserted into the chamber through the second or proximal end of the barrel. The paddle extends to the first or distal end of the barrel. Grooves or ducts are formed on the paddle so that rotation of the paddle results in efficient mixing of the components within the chamber.

After the multi-component composition is mixed, the paddle is removed from the syringe barrel and the plunger is then inserted within the second end of the barrel. Optionally, a scraper member having adjacent arms that extend into the chamber and engage opposing sides of the paddle, can be inserted into the access port prior to removal of the paddle. As the paddle is withdrawn from the barrel, the arms scrape the composition off the sides of the paddle, retaining the composition within the barrel. After the paddle member is withdrawn and the scraper is removed, the plunger is inserted through the proximal or second end of the syringe barrel. Here, again, as the plunger is advanced, the air between the plunger and the composition is pushed out of the chamber through the access port. Once the plunger passes the access port, the remaining composition is pushed out a nozzle located at the first end of the barrel.

The above described syringe and method of use provides several benefits and improvements over the prior art. By way of example and not by limitation, since the components are mixed in the syringe, the composition does not have to be later transferred to the syringe. Furthermore, rotationally mixing the composition within the chamber minimizes the amount of air that gets entrained within the composition. Furthermore, the side access port provides several advantages. Most importantly, the access port enables easy delivery of the components to the first or distal end of the syringe and allows air to escape as the plunger is advanced within the chamber.

BRIEF DESCRIPTION OF THE DRAWINGS

In order that the manner in which the above-recited and other advantages and objects of the invention are obtained will be understood, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention is directed to methods and apparatus for dispensing compositions such as dental cements or impression materials. More particularly, the present invention is directed to methods and apparatus for dispensing compositions such that the compositions are substantially free from entrained air.

Figure 1:
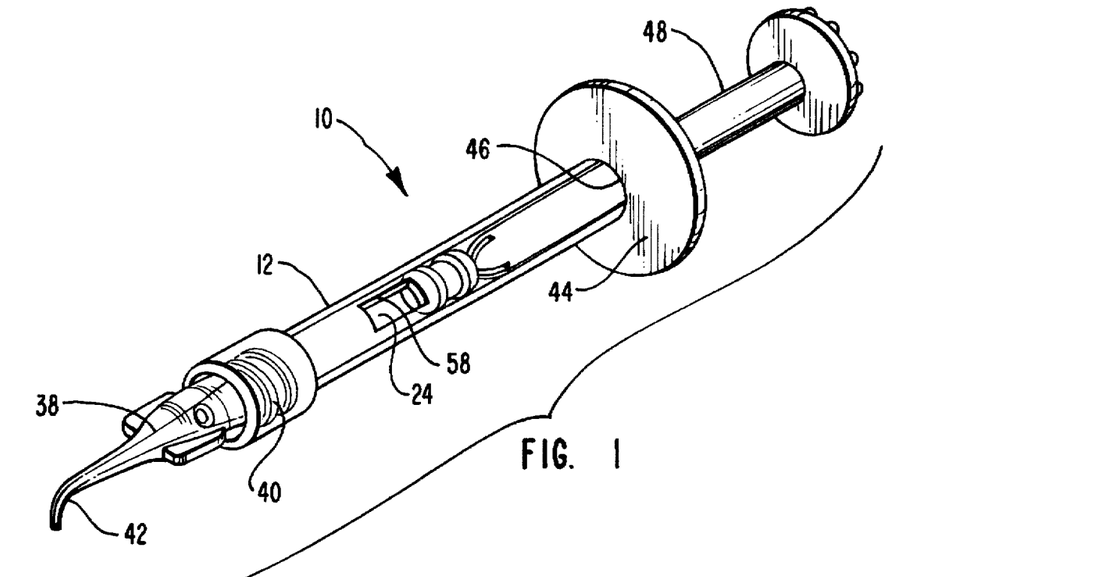
FIG. 1 is a perspective view of a syringe assembly having a barrel with an access port extending through a sidewall thereof.

FIG. 1 illustrates a syringe assembly 10 useful for dispensing compositions, such as dental cements and bonding materials in accordance with the present invention. Syringe assembly 10 includes a hollow, elongated barrel 12 having a nozzle 38 attached at one end and a plunger 48 slidably received in the opposing end. As better shown in FIG. 2, barrel 12 includes a first or distal end 14, and opposing second or proximal end 16 and a substantially cylindrical sidewall 18 extending therebetween. Sidewall 18 has an exterior surface 20 and an interior surface 22. Interior surface 22 defines a substantially cylindrical chamber 24 for holding the composition.

Figure 2:
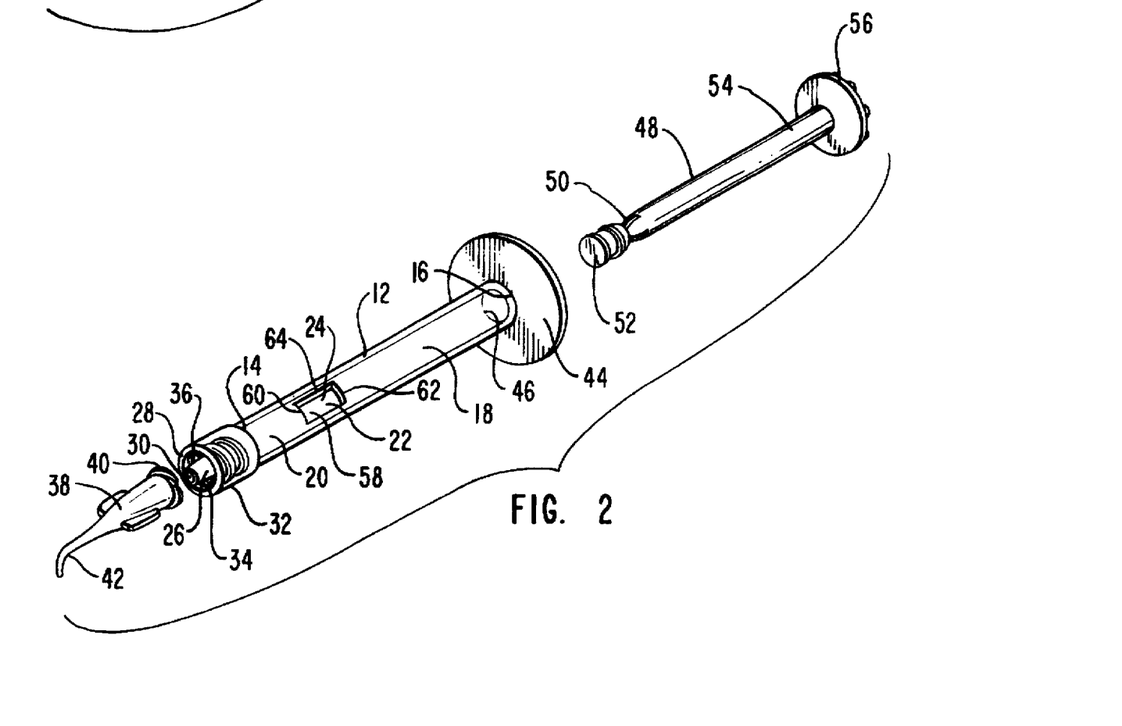
FIG. 2 is an exploded view of the syringe assembly shown in FIG. 1.

In the preferred embodiment as shown in FIG. 2, a tapered exit tube 26 projects from first end 14. Exit tube 26 has an interior surface 28 defining an exit port 30 that longitudinally extends through exit tube 26 and communicates with chamber 24 at first end 14. Surrounding exit tube 26 is an attachment sleeve 32. Attachment sleeve 32 has an interior surface 34 with engagement threads 36 positioned thereon.

Nozzle 38 is configured to selectively attach in fluid communication with exit tube 26. To accomplish this end, nozzle 38 has a threaded end 40 for engagement with threads 36 of attachment sleeve 32. Opposite threaded end 40 is a flexible and angled spout 42 for guiding delivery of the composition to a desired location. It is, of course, envisioned that different sizes and shapes of spouts 42 can be used depending on the type and intended use of the composition. Furthermore, in alternative embodiments, nozzle 38 could be permanently attached to first end 14 or means other than threads could be used to attach different sizes and/or shapes of nozzles.

Radially extending outward at second end 16 of barrel 12 is an annular flange or handle 44 that encircles barrel 12. Handle 44 is used in the advancement of plunger 48. As shown in FIG. 2, an opening 46 extends through handle 44 and into chamber 24 at second end 16. The present invention also provides piston means receivable in chamber 24 at second end 16 of barrel 12 for advancing the composition positioned within barrel 12 through exit port 30 at first end 14. By way of example, and not by limitation, the piston means comprises an elongated plunger 48 as depicted in FIGS. 1 and 2.

Plunger 48 has a lead or distal end 50 and an opposing tail or proximal end 54. Positioned at lead end 50 is a sealing gasket 52. Radially extending outward at tail end 54 is an annular top 56 used in advancing plunger 48. Plunger 48 is sized to be slidably received within chamber 24 through opening 46 at second end 16. Plunger 48 also has a length that permits gasket 52 to be selectively advanced within the entire length of chamber 24, such that gasket 52 abuts the distal end 14 of chamber 24 when plunger 48 is fully inserted into chamber 24. Gasket 52 is made of a soft, compressible, sealing material, such as rubber, which allows the outer periphery of gasket 52 to seal against interior surface 22 of chamber 24 as plunger 48 is advanced within chamber 24. In alternative embodiments, the piston means can take the form of any size or shape of conventional plunger used with a conventional syringe.

Referring again to FIG. 2, the present invention also provides an access port 58 extending through sidewall 18 to communicate with chamber 24. In a preferred embodiment, access port 58 is substantially rectangular having a first edge 60, an opposing second edge 62, and side edges 64. In alternative embodiments, access port 58 can be any configuration such as circular, triangular, or square. Access port 58 is preferably positioned and configured so that the composition can be delivered through access port 58 and into chamber 24 at first end 14.

The exact location of access port 58 relative to the longitudinal axis of chamber 24 depends on the desired unit dose to be administered from the syringe. For example, where the desired unit dose is approximately 3 milliliters, the access port 58 is positioned on the syringe such that the volume of that portion of chamber 24 beginning at the first edge 60 of access port 58 and extending to the distal end 14 of chamber 24 is approximately 3 milliliters. Thus, a variety of syringes designed for a variety of unit dosages can be produced simply by changing the position of access port 58 relative to the distal end 14 of syringe barrel 12.

Figure 3:
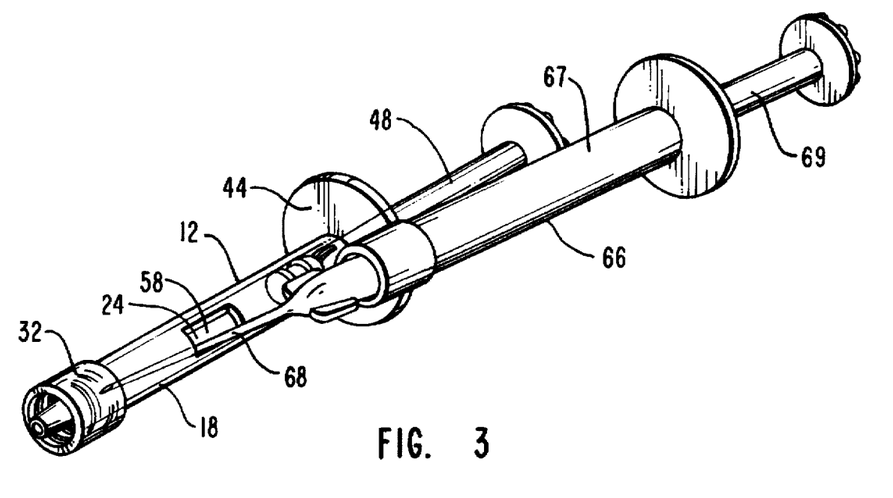
FIG. 3 is a perspective view of a filling syringe delivering a composition to the syringe in FIG. 1 through the access port.

As depicted in FIG. 3, a filling syringe 66 is used to position the composition within chamber 24. Filling syringe 66 has a barrel 67 for holding the composition, a plunger 69 for advancing the composition, and a elongated, rigid, filling tube 68 for directing the composition. That is, by inserting filling tube 68 through access port 58 so that the end of filling tube 68 extends to first end 14 near exit port 30, the composition contained within filling syringe 66 can be delivered into chamber 24.

When filling syringe 66 is used, it is preferred to have exterior surface 20 adjacent to second edge 62 of access port 58 substantially flat so as to allow a straight and unobstructed positioning of filling tube 68 within chamber 24. The term "flat" as used in the specification is defined to mean the absence of any obstructions rising from exterior surface 20. Exterior surface 20 can be cylindrical in shape and still be flat. In alternative embodiments, any conventional means or device can be used to position the composition within chamber 24. Depending on the device or method used, however, the size and position of access port 58 may have to be varied to best insure that the composition is positioned at first end 14.

Figure 4:
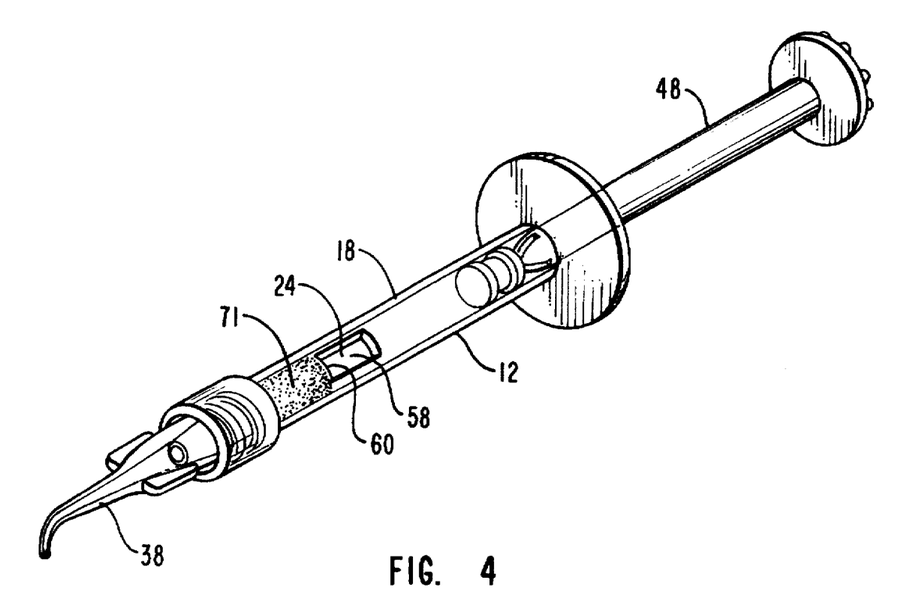
FIG. 4 is a perspective view of the syringe in FIG. 3 having the composition field to the access port.

It is preferred to start positioning the composition at first end 14 so as to avoid trapping air bubbles within chamber 24. As the composition is delivered, filling syringe 66 is slowly removed so, as shown in FIG. 4, chamber 24 is filled with composition 71, beginning at first or distal end 14 and working back toward access port 58, filling the distal end 14 of chamber 24 to a point proximate to first edge 60 of access port 58. The positioning of access port 58 is dependent upon how much composition needs to be delivered from syringe system 10. That is, where more composition needs to be delivered, barrel 12 can be formed having access port 58 positioned closer to second end 16. Alternatively, where less composition is needed, access port 58 can be formed closer to first end 14. Once the composition is positioned within barrel 12, plunger 48, positioned within chamber 24 at second end 16, is advanced towards first end 14. In so doing, air within chamber 24 at second end 16 is pushed out through access port 58.

Figure 5:
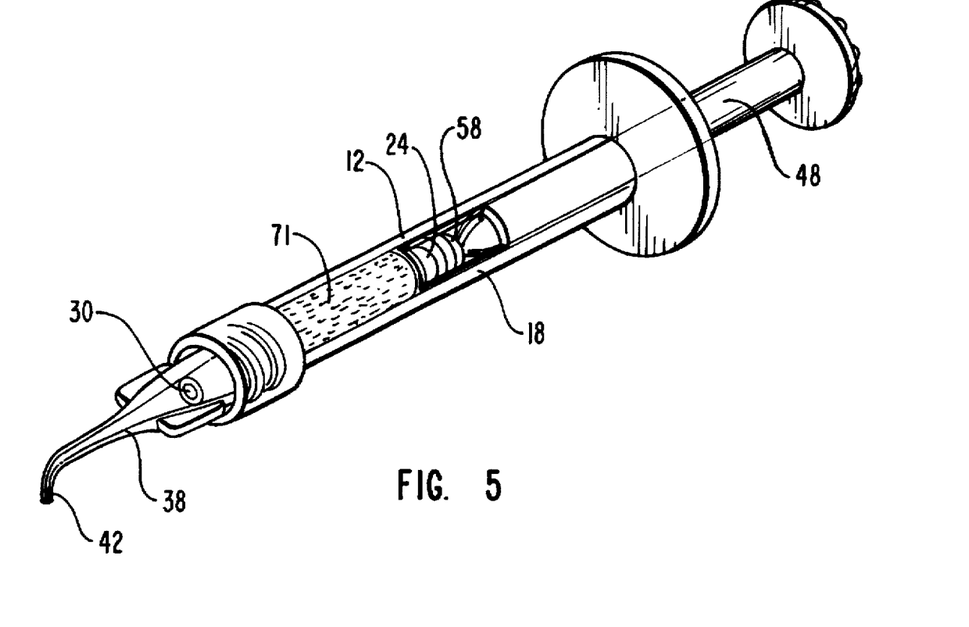
FIG. 5 is a perspective view of the syringe in FIG. 4 having a plunger advanced to the composition at the access port.

It can be appreciated that it is preferred to have the composition filled at least to first edge 60 of access port 58 is to prevent air from being trapped between composition 71 and plunger 48. It is possible to have the composition filled higher than first edge 60, however, a portion of the composition may spill out through access port 58 as plunger 48 is advanced. As previously mentioned, it is also preferred to have access port 58 rectangular so that first edge 60 is perpendicular to the longitudinal axis of barrel 12. This configuration helps to ensure all of the air is removed as plunger 48 is advanced and provides a clear line as to where the composition needs to be filled. Once the plunger passes access port 58, as depicted in FIG. 5, the composition is pressed through exit port 30 and through nozzle 38 so as to be delivered through spout 42.

The present invention also provides methods and apparatus for mixing and dispensing multi-component compositions such as dental cements or impression materials. More particularly, the present invention also provides syringe mixing and dispensing systems useful for rapid and complete mixing of multi-component compositions and subsequent dispensing of the mixed compositions without the entrainment of air and without the necessity of having to mix the multi-component composition in one container and then having to transfer the mixed composition from the mixing container into the syringe.

It is frequently desirable to mix together various components of multi-component compositions, such as some dental cements and bonding materials. For purposes of brevity, the discussion contained herein shall be principally directed to the use of two-component systems, sometimes referred to as A and B component systems. Nevertheless, it should be understood that the methods and apparatus of the present invention will accommodate systems having more than two components.

The system for mixing and dispensing the multi-components compositions of the present invention includes syringe 10 as discussed previously in FIGS. 1–5. Mixing of the components is performed by initially positioning the discrete components within first end 14 of chamber 24. It has been determined that the most effective mixing of the A and B components utilizing the apparatus of the present invention is accomplished by loading the two components side-by-side within syringe barrel 12 rather than one on top of the other. Side-by-side loading may be advantageously performed by use of a two-syringe device 90, such as that shown in FIG. 6. Two-syringe device 90 includes two syringe barrels 92A and 92B coupled together by clamps 94A, 94B and 94C. Each of syringe barrels 92 A and B has an output end 96A and 96B with a nozzle 98A and 98B secured thereto. In turn, each nozzle 98A and 98B is provided with an elongated tubing member 100A and 100B for directing placement of the individual components. A collar 102 is used to secure tubing members 100A and 100B together, with both tubing members terminating at the same distal end 101.

Figure 6:
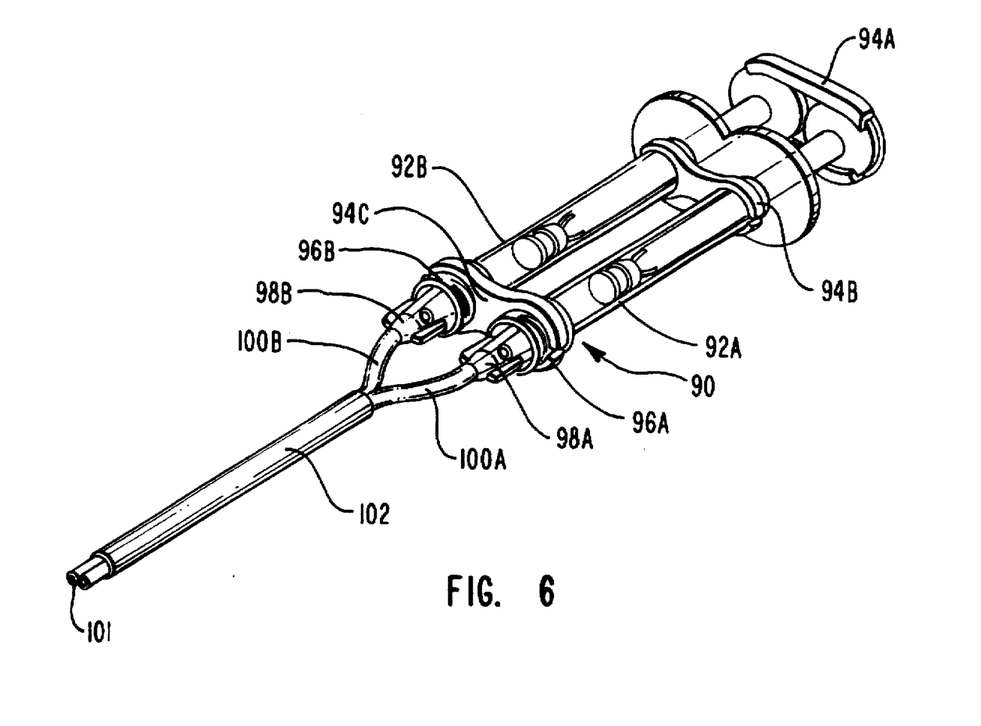
FIG. 6 is a perspective view of a multi-syringe device for use in introducing two components of a two-part composition into the syringe in FIG. 1 for subsequent mixing therein.

Prior to use, the syringe barrels 92A and 92B of FIG. 6 are filled with A and B components, respectively, of a two-component composition. First end 14 of syringe barrel 12 is sealed with a cap, such as the cap 104 illustrated in FIG. 8. Tubing members 100A and 100B are then inserted through access port 58 so that distal end 101 is positioned adjacent to exit port 30 at first end 14. The two plungers 93A and 93B are then simultaneously depressed while slowly withdrawing tubing members 100A and 100B from within syringe barrel 12. This results in placement of material from each of syringe barrels 92A and 92B side-by-side within first end 14 of chamber 24. This process is accomplished in substantially the same way as discussed with FIGS. 3 and 4 except that now two components are being filled within chamber 24.

It should be understood that additional syringe barrels 92 and associated components could be added to the device of FIG. 6 in order to accommodate more than two components. Further, the diameters of syringe barrels 92A and 92B could be altered as necessary to effect differing ratios of A and B components. For example, if A and B components are to be added in substantially equal amounts, both syringe barrels 92A and 92B would be substantially identical. If, however, it were desired to add two parts of A to one part of B, syringe barrel 92A should have a cross-sectional area twice that of syringe barrel 92B. It will be appreciated that other modifications could be made in the respective sizes of syringe barrels 92A and 92B to accommodate other mixing ratios. Markings on the sides of syringe barrels 92A and 92B can be used to measure a desired volume to be introduced into syringe barrel 12, or one could look at markings optionally provided on syringe barrel 12.

Figure 7:
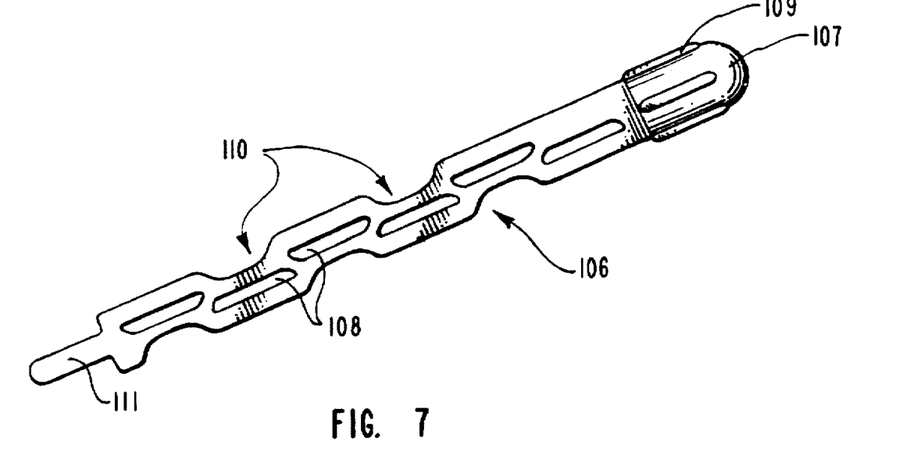
FIG. 7 is a perspective view of a paddle used for mixing a two-part composition within the syringe of FIG. 1.
Figure 8:
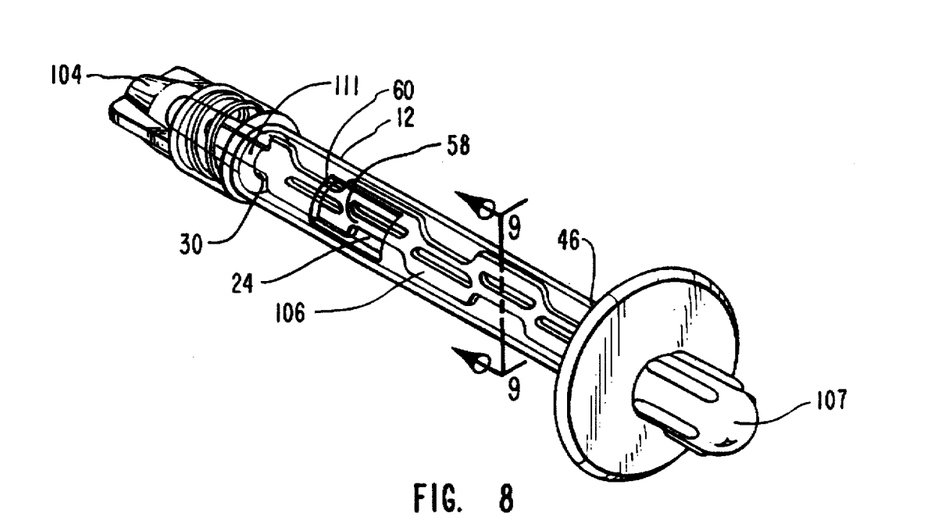
FIG. 8 is a perspective view of the paddle in FIG. 7 being inserted within the syringe for mixing of the components.

The present invention also provides blending means selectively inserted within chamber 24 for mixing the components of the composition within first end 14 of barrel 12. As depicted in FIG. 7, one embodiment of the blending means comprises an elongate paddle 106 having a rotation knob 107 with finger grips 109 positioned at one end. A rotation pin 111 is positioned at the opposing end of paddle 106. During use, as shown in FIG. 8, paddle 106 is inserted within chamber 24 through opening 46 such that rotation pin 111 is inserted within exit port 30. Paddle 106 has a length slightly longer than chamber 24 so that rotation knob 107 projects out of second end 16 when rotation pin 111 is inserted within exit port 30. Once paddle 106 is properly positioned, rotation of knob 107 causes paddle 106 to rotate within chamber 24, thereby mixing the components into a homogeneous composition.

Figure 9:
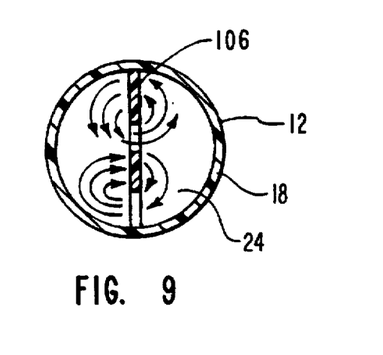
FIG. 9 is a cross-sectional view taken along lines 9—9 of FIG. 8 showing in schematic form by use of arrows how the paddle mixes the composition within the syringe.

The width of paddle member 106 is preferably about the same as the internal diameter of chamber 24. This sizing enables more complete mixing by scraping material from interior surface 22 of syringe barrel 12. As illustrated in FIG. 7, it is presently preferred that paddle 106 be provided with a plurality of internal cutouts 108 and 110 from the body of paddle 106. The provision of cutouts 108 and 110 generate turbulence as paddle 106 is rotated. The cutouts function as means for effecting turbulence within chamber 24 in order to obtain more rapid and complete mixing. Such mixing can be accomplished with little or no entrainment of air bubbles. FIG. 9 illustrates in schematic form the generation of turbulence in response to rotation of paddle. It should be understood that the cutouts 108 and 110 are needed only in the region where mixing occurs. Thus, the size of paddle 106 and the location of cutouts 108 and 110 depends on the desired unit dose.

Figure 10:
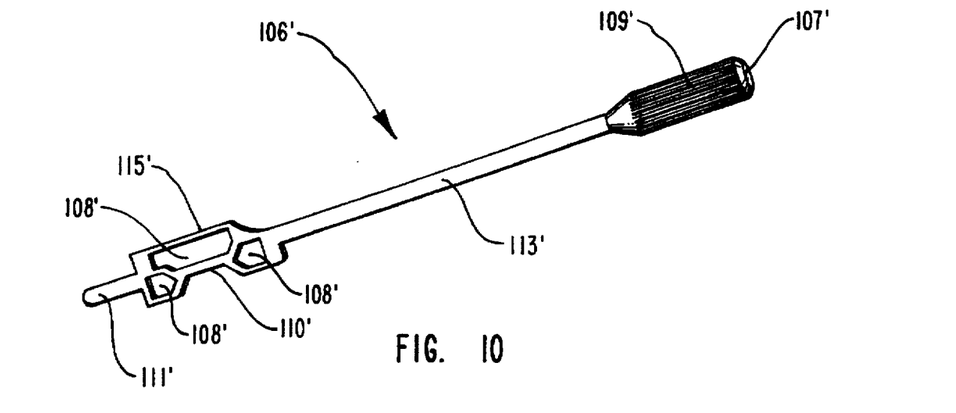
FIG. 10 is a perspective view of anther presently preferred embodiment of the paddle used to mix a multi-component composition within the syringe of FIG. 1.

Alternative embodiments of the elements of the apparatus of the present invention may be made as long as the broad functions set forth above are preserved. One of ordinary skill will be able to envision many other workable alterations in light of the teachings herein. For example, another presently preferred embodiment of the mixing paddle is shown in FIG. 10. As illustrated in FIG. 10, paddle 106' has a rotation knob 107', an elongated stem 113', and an enlarged, substantially planar mixing portion 115'. Rotation knob 107' has a knurled surface 109' to facilitate ease of gripping and rotation of knob 107'. Mixing portion 115' has a plurality of cutouts 108' and 110' that generate turbulence, in a manner similar to that described above in relation to the paddle illustrated in FIGS. 7–9, as paddle 106' is rotated. As mentioned previously, the cutouts function as means for effecting turbulence within chamber 24 in order to obtain more rapid and complete mixing, which is achieved with little or no entrainment of air bubbles.

In one embodiment of the present invention, scraper means can be used for removing material from the surface of paddle 106 after mixing is completed. One embodiment of the scraper means is illustrated in FIG. 10. Scraper 120 has an interior surface 122, an exterior surface 124 and is configured comparable to the size and shape of access port 58. Positioned on exterior surface 124 is a handle 126. Projecting from interior surface 122 are a pair of adjacent arms 128 that terminate at distal ends 130. Arms 128 are positioned to extend into chamber 24 and snugly fit on opposing sides of paddle 106. Once mixing of the composition is completed, handle 126 is used to grasp scraper 120 and insert arms 128 through access port 58 and onto opposing sides of paddle 106. As paddle 106 is removed from chamber 24, arms 128 remove the composition from off paddle 106. Arms 128 are preferably sized so that distal ends 130 of arms 128 are biased against interior surface 122 of chamber 24. This configuration gives greater support to arms 128 during removal of paddle 106. After paddle 106 is removed, scraper 120 can also removed and plunger 48 inserted.

Once the scraper means is removed and plunger 48 inserted, delivery of the mixed composition through nozzle 38 is performed by advancement of plunger 48. This process is performed in substantially the same manner as previously discussed with FIGS. 4 and 5.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Letters Patent is:

1. A syringe for dispensing a composition so that the composition is substantially free from entrained air, the syringe comprising:
   (a) a hollow elongated barrel having:
      (i) a first end with an exit port extending therethrough;
      (ii) an open second end opposite the first end;
      (iii) a sidewall extending between the first end and the opposing second end, the sidewall having an interior surface defining a chamber for holding the composition; and
      (iv) an access port extending through the sidewall to communicate with the chamber, the access port being configured so that the composition can be delivered through the access port and into the chamber at the first end; and (b) piston means receivable in the chamber at the second end of the barrel for advancing the composition positioned within the barrel through the exit port at the first end of the barrel.

2. A syringe as recited in claim 1, wherein the access port has a first edge positioned towards the first end of the barrel, the first edge being substantially perpendicular to the longitudinal axis if the barrel.

3. A syringe as recited in claim 1, wherein the access port is substantially rectangular.

4. A syringe as recited in claim 1, wherein the syringe has a nozzle secured to first end of the barrel.

5. A syringe as recited in claim 1, wherein the barrel has an exterior surface, at least a portion of the exterior surface being substantially flat adjacent to the access port.

6. A syringe as recited in claim 1, wherein the piston means comprises a plunger slidably received within the chamber at the second end of the barrel.

7. A syringe as recited in claim 1 further comprising blending means selectively inserted within the chamber for mixing the components of the composition within the first end of the syringe barrel.

8. A syringe as recited in claim 7, wherein the blending means comprises an elongated paddle member for insertion into the chamber.

9. A syringe as recited in claim 7, wherein the blending means further comprises a knob positioned at one end of the paddle to facilitate rotation of the paddle.

10. A syringe as recited in claim 7, wherein the elongated paddle includes:
 (a) a length that extends at least between the first end and the second end of the chamber; and
 (b) a width that substantially spans across the inner diameter of the chamber.

11. A syringe as recited in claim 7, wherein the elongated paddle includes means for effecting turbulence in order to assist in mixing the discrete components positioned within the chamber.

12. A syringe as recited in claim 11, wherein the means for effecting turbulence comprises cutouts in the paddle member.

13. A syringe as recited in claim 7 further comprising scraper means for removing the composition from the blending means so as to retain the composition within the chamber upon removal of the blending means after mixing is complete.

14. A system as recited in claim 13, wherein the scraper means comprises a scraper having two projecting fingers for insertion through the access chamber on opposing sides of the blending means for removing the composition from the blending means as the blending means is removed from the chamber.

15. A syringe for dispensing a composition so that the composition is substantially free from entrained air, the syringe comprising:
 (a) a hollow elongated barrel having:
  (i) a first end;
  (ii) an open second end opposite the first end;
  (iii) a sidewall extending between the first end and the opposing second end, the sidewall having an exterior surface and an interior surface defining a chamber for holding the composition; and
  (iv) an access port extending through the sidewall to communicate with the chamber, wherein the access port is substantially rectangular having a first edge positioned towards the first end of the barrel and wherein the first edge is substantially perpendicular to the longitudinal axis of the barrel so that the composition can be directly delivered through the access port and into the chamber at the first end;
 (b) a nozzle positioned at the first end and having a passageway extending therethrough to communicate with the chamber;
 (c) blending means selectively inserted within the chamber for mixing the components of the composition within the first end of the syringe barrel; and
 (d) a plunger slidably received within the chamber at the second end of the barrel, the plunger being configured to selectively advance the composition positioned within the barrel through the nozzle at the first end of the barrel.

16. A syringe as recited in claim 15 further comprising scraper means for removing the composition from the blending means so as to retain the composition within the chamber upon removal of the blending means after mixing is complete.

17. A system as recited in claim 16, wherein the scraper means comprises a scraper having two projecting fingers for insertion through the access chamber on opposing sides of the blending means for removing the composition from the blending means as the blending means is removed from the chamber.

18. A method for dispensing a composition from a syringe so that the composition is substantially free from entrained air, the method comprising the steps of:
 (a) obtaining a hollow elongated barrel having:
  (i) a first end with an exit port extending therethrough;
  (ii) an open second end opposite the first end;
  (iii) a sidewall extending between the first end and the opposing second end, the sidewall having an interior surface defining a chamber for holding the composition; and
  (iv) an access port extending through the sidewall to communicate with the chamber;
 (b) depositing the composition through the access port to the first end of the barrel so that the composition fills the chamber to the access port;
 (c) advancing a plunger from the second end of the barrel to the composition in the chamber so that air within the chamber is evacuated through the access port; and
 (d) further advancing the plunger so that the composition is delivered through the exit port at the first end of the barrel, the composition being substantially free of entrained air.

19. A method as recited in claim 18 further comprising, after the depositing step, the step of mixing the composition within the chamber.

20. A method as recited in claim 19, wherein the mixing step comprises the steps of:
 (a) inserting a paddle into the chamber through the second end of the chamber;
 (b) rotating the paddle to mix the composition; and
 (c) removing the paddle from the chamber.

21. A method as recited in claim 20, wherein the mixing step further comprises:
 (a) obtaining a scraper having a pair of adjacently disposed arms;
 (b) inserting the scraper through the access port after the composition has been mixed so that the arms engage opposing sides of the paddle; and
 (c) sliding the paddle out the second end of the chamber so that the arms of the scraper remove the composition from the paddle.

* * * * *

UNITED STATES PATENT AND TRADEMARK OFFICE
CERTIFICATE OF CORRECTION

PATENT NO. : 5,697,903

DATED : Dec. 16, 1997

INVENTOR(S) : Dan E. Fischer

It is certified that error appears in the above-identified patent and that said Letters Patent is hereby corrected as shown below:

Please add the following U.S. Patent Documents to References Cited:

| | | |
|---|---|---|
| 2,129,983 | 9/1938 Bacon | 128/214 |
| 2,489,600 | 11/1949 Tydings et al. | 128/220 |
| 4,581,015 | 4/1986 Alfano | 604/88 |
| 4,698,055 | 10/1987 Sealfon | 604/82 |

Col. 6, line 16, before "to prevent" change "is" to --in order--

Col. 6, line 62, after "barrels" change "92 A and B" to --92A and 92B--

Col. 7, line 37, after "comprises an" change "elongate" to --elongated--

Figure 11:
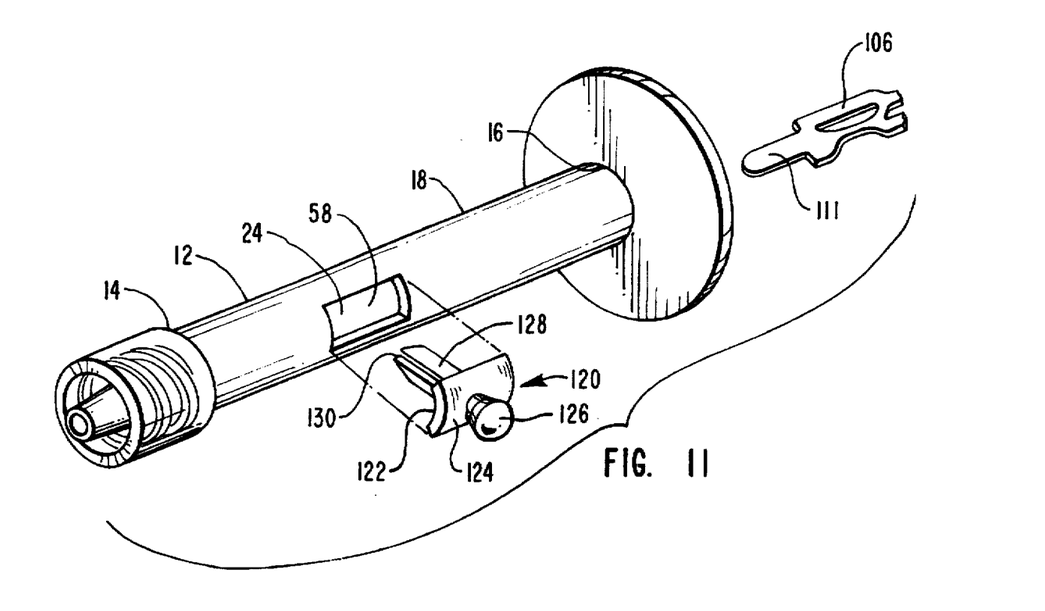
FIG. 11 is a partially exploded perspective view of a scraper that is selectively inserted within the access port of the syringe in FIG. 1.

Col, 8, line 19, change "FIG. 10" to --FIG. 11--

Col. 8, line 35, after "can also" insert --be--

Col. 9, line 8, after "axis" change "if" to --of--

Signed and Sealed this

Twenty-fifth Day of August, 1998

*Attest:*

BRUCE LEHMAN

*Attesting Officer*              *Commissioner of Patents and Trademarks*